United States Patent [19]

Broger et al.

[11] Patent Number: 5,360,908

[45] Date of Patent: Nov. 1, 1994

[54] ISOQUINOLINE DERIVATIVES

[75] Inventors: Emil A. Broger, Magden, Switzerland; Bernd Heiser, Inzlingen, Germany

[73] Assignee: Hoffman-LaRoche Inc., Nutley, N.J.

[21] Appl. No.: 766,463

[22] Filed: Sep. 26, 1991

Related U.S. Application Data

[63] Continuation of Ser. No. 518,581, May 1, 1990, abandoned.

[30] Foreign Application Priority Data

May 10, 1989 [CH] Switzerland .................. 1751/89
Mar. 16, 1990 [CH] Switzerland .................. 864/90

[51] Int. Cl.⁵ .................. C07D 217/16; C07D 217/24
[52] U.S. Cl. ................................................. 546/146
[58] Field of Search .................................. 546/146

[56] References Cited

U.S. PATENT DOCUMENTS

| | | | |
|---|---|---|---|
| 4,727,147 | 2/1988 | Wintermeyer et al. | 546/149 |
| 4,851,537 | 7/1989 | Noyori et al. | 546/146 |
| 4,857,648 | 8/1989 | Broger et al. | 546/146 |
| 4,954,644 | 9/1990 | Sayo et al. | 556/14 |

OTHER PUBLICATIONS

Lenz, et al., "J. Org. Chem.", vol. 53, No. 6, 1988, pp. 1176-1183.
Kitamura, et al., "Chemical Abstracts", vol. 111, 1989, Col.111:134625b.
Broger, et al. (II), "Chemical Abstracts," vol. 112, 1990, col. 112.20914k.

*Primary Examiner*—C. Warren Ivy
*Assistant Examiner*—D Margaret M. Mach
*Attorney, Agent, or Firm*—George M. Gould; William H. Epstein; Catherine A. Picut

[57] ABSTRACT

A process for the preparation of isoquinoline derivatives of the formulas

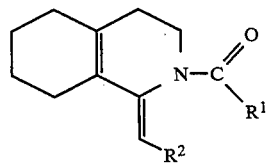

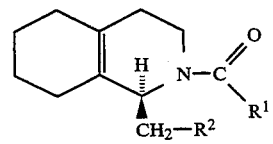

wherein $R^1$ and $R^2$ have the significances herein after set forth in the description, is described.

The compounds of formula IV are obtained by asymmetrically hydrogenating the compounds of formula I. The compounds of formula I are, in turn, obtained by isomerizing compounds of the formulas

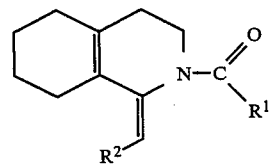

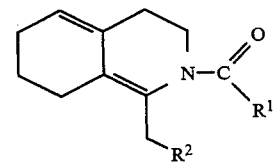

or a mixture of compounds of the formulas (Abstract continued on next page.)

E-form II
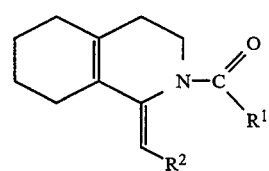
Z-form I
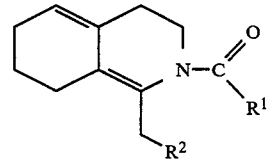
III
14 Claims, No Drawings

ISOQUINOLINE DERIVATIVES

This is a continuation, of application Ser. No. 07/518,581 filed May 1, 1990 now abandoned.

BRIEF SUMMARY OF THE INVENTION

The invention relates to a process for the preparation of isoquinoline derivatives which are valuable intermediates in the synthesis of dextromethorphan. The process comprises isomerizing

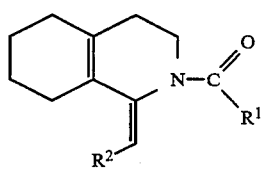

E-form II or

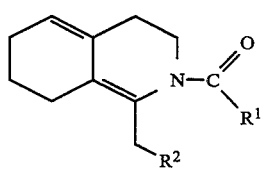

III or a mixture of isoquinoline derivatives of the formulas

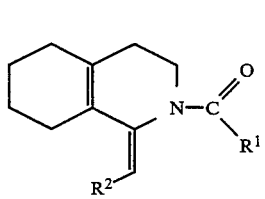

E-form II

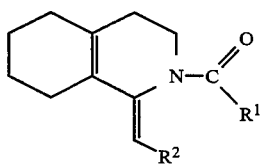

Z-form I

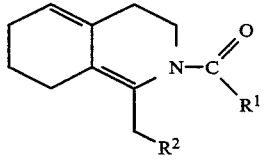

III wherein $R^1$ is lower alkyl, aryl or aryl-lower alkyl and $R^2$ is phenyl or p-methoxy-substituted phenyl, and, if desired, asymmetrically hydrogenating a thus-obtained isoquinoline derivative of the formula in the Z-form

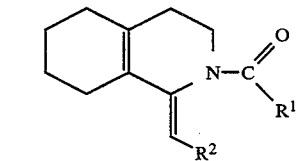

I wherein $R^1$ and $R^2$ have the above significance, to give a compound of the formula

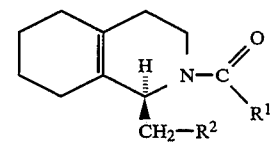

IV wherein $R^1$ and $R^2$ have the above significance.

DETAILED DESCRIPTION OF THE INVENTION

The process of the invention comprises isomerizing

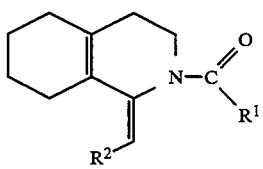

E-form II or

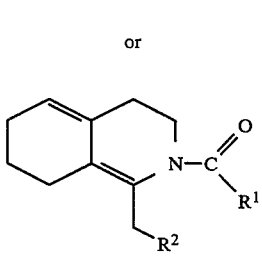

III or a mixture of isoquinoline derivatives of the formulas

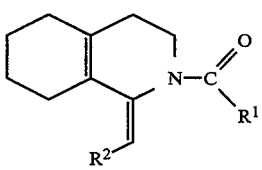

E-form II

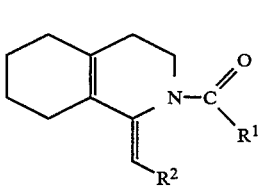

Z-form I

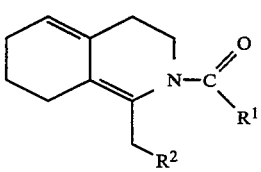

III wherein $R^1$ is lower alkyl, aryl or aryl-lower alkyl and $R^2$ is phenyl or p-methoxy-substituted phenyl, and, if desired, asymmetrically hydrogenating a thus-obtained isoquinoline derivative of the formula in the Z-form

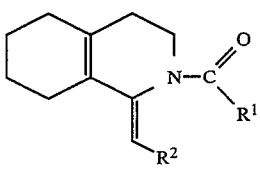

I wherein R¹ and R² have the above significance, to give a compound of the formula

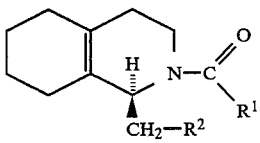

IV wherein R¹ and R² have the above significance.

As used herein, the term "lower alkyl" denotes straight-chain or branched alkyl groups having 1 to 8 carbon atoms, for example, methyl, ethyl, n-propyl, isopropyl, butyl, tert. butyl, pentyl, hexyl, heptyl, octyl and the like. The term "aryl" denotes unsubstituted or substituted phenyl or naphthyl.

The term "aryl-lower-alkyl" denotes groups in which the aryl residue has the foregoing significance and the lower alkyl residues are groups having 1 to 3 carbon atoms, for example, benzyl and the like.

In the present invention, the symbol " ▌ " denotes that the corresponding substituent is situated above the plane of the molecule and the symbol " ≡ " denotes that the corresponding substituent is situated below the plane of the molecule.

In connection with the ligands of formulas VI and VII, the mentioned phenyl and benzyl residues can be not only unsubstituted, but also substituted in the ortho-, meta-or para-position as well as multiply-substituted. As substituents, there come into consideration here lower alkyl or lower alkoxy groups, preferably, methyl or methoxy groups, or also di-lower alkylamino groups, preferably dimethylamino groups, as well as fluorine. The term "lower alkyl" denotes in this connection straight-chain or branched alkyl groups having 1 to 4 carbon atoms such as methyl, ethyl, propyl, isopropyl, n-butyl, isobutyl and tert. butyl. The terms "lower alkoxy", "di-lower alkyl- amino" and "lower alkoxycarbonyl" denotes groups in which the alkyl residue has the foregoing significance. As protecting groups for the hydroxymethyl group, there especially come into consideration in the scope of the invention the usual ether-forming groups, for example,benzyl, methyl, tert. butyl, methoxymethyl and the like as well as ester-forming groups, for example, acetyl, benzoyl and the like.

The isomerization of a compound of formula II (E-form) or III or of a mixture of isoquinoline derivatives of formulas II (E-form), I (Z-form) and III can be carried out not only by heating in a chlorinated hydrocarbon or in a solvent which contains a chlorinated hydrocarbon, but also catalytically.

The heating in a chlorinated hydrocarbon or in a solvent which contains a chlorinated hydrocarbon can be effected at a temperature of about 50° C. to about 200° C., preferably of about the reflux temperature to about 150° C. and if necessary under pressure. As chlorinated hydro-carbons, there can be used those which are usually used as solvents, for example, methylene chloride, chloroform, 1,2-dichloroethane and the like.

As solvents, there can be used in this connection especially lower alkanols having 1 to 5 carbon atoms, for example, methanol, ethanol, propanol and the like. Methanol which contains methylene chloride is a preferred solvent containing a chlorinated hydrocarbon.

The catalytic isomerization can be carried out in an inert organic solvent at a temperature in the range from about −10° C. to about 150° C., if necessary under the pressure of an inert gas. The isomerization is, however, preferably effected at a temperature in the range from about room temperature to about 120° C. As inert organic solvents, there can be used here aromatic hydrocarbons, for example, benzene or toluene, alcohols having 1-3 C atoms for example methanol, ethanol or propanol, ethers for example, as tetrahydrofuran or dioxane or also chlorinated hydrocarbons, for example, methylene chloride, chloroform, 1,2-dichloroethane and the like. Furthermore, mixtures of these solvents can be used. The usual isomerization catalysts can be used as catalysts for this catalytic isomerization. As examples of such catalysts, there can be named acids such as hydrogen halides, for example, hydrogen chloride or hydrogen bromide, sulfonic acids, for example, p-toluenesulfonic acid, sulfinic acids, for example, phenylsulfinic acid, sulfuric acid, nitric acid, Lewis acids, for example, BF₄, TiCl₁₄ and the like, as well as carboxylic acids for example, acetic acid or propionic acid and the like. Furthermore, there can also be named iodine, 2,2,6,6-tetramethylpiperidyloxyl as well as transition metal complexes, such as, rhodium complexes, for example, RhCl₃ hydrate; ruthenium complexes for example, RuCl₃ hydrate; and palladium complexes such as, for example, PdCl₂(CH₃CN)₂ and the like.

By the asymmetric hydrogenation of the isoquinoline derivatives of formula I in the Z-form, there are obtained those of the formula

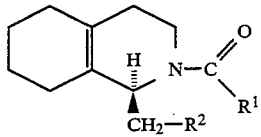

IV wherein R¹ and R² have the above significance.

The asymmetric hydrogenation can be carried out in a known matter. In particular, the hydrogenation can be carried out in the presence of a ruthenium catalyst of formula V or Va:

V or

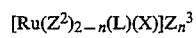

Va wherein Z is halogen or a residue of the formula A-COO⁻, in which A is lower alkyl, aryl, halogenated lower alkyl or halogenated aryl, Z² is halogen, X is benzene, hexamethylbenzene or p-cymene, Z³ is halogen, BF₄, ClO₄ or B(phenyl)₄, n is the number 1 or 2 and L is a ligand of formula VI or VII:

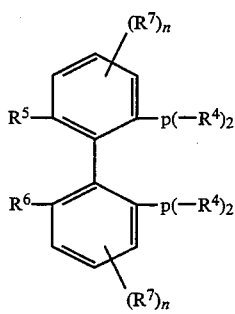

VI wherein R⁴ is phenyl R⁵ and R⁶, which can be the same or different, are hydrogen, lower alkyl, lower alkoxy, di-lower alkylamino or protected hydroxymethyl or R⁵ and R⁶ taken together are the group

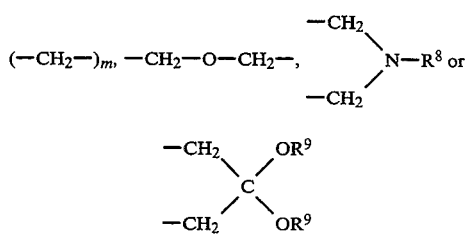

in which m is a number from 3 to 5, R⁸ is lower alkyl phenyl or benzyl and R⁹ is lower alkyl or both R⁹'s taken together are di- or trimethylene, R⁷ is methyl, lower alkoxy, di-lower alkylamino or fluorine and n is the number 0, 1, 2 or 3;

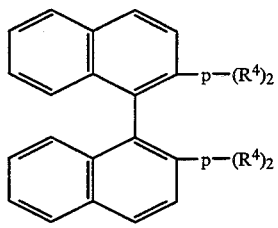

VII wherein R⁴ has the above significance and the naphthalene rings are unsubstituted or substituted in the ortho-position with methyl, ethyl, halogen, di-lower alkylamino or lower alkoxy.

The term "halogen" denotes fluorine, chlorine, bromine or iodine.

The term "halogenated lower alkyl" denotes lower alkyl groups having a variable number of halogen atoms, especially chlorine or fluorine, whereby a halogen atom is preferably situated in the α-position to the —COO⁻ group.

Preferred halogenated lower alkyl groups are perfluorinated and perchlorinated lower alkyl groups, for example trifluoromethyl, pentafluoroethyl and the like. Halogen is fluorine, chlorine, bromine or iodine, especially fluorine or chlorine. The term "halogenated aryl" preferably is perfluorophenyl or perfluoro- biphenyl.

Preferred ligands are those of formula VI. Of these there are, furthermore, preferred those in which R⁴ is unsubstituted or methyl-substituted phenyl, R⁵ and R⁶ are the same and are lower alkyl or taken together are the group —CH₂—O—CH₂—, n is the number 0 or 1 and R⁷ is methyl, fluorine or di-lower alkylamino.

When n is the number 1, the substituent R⁷ is preferably situated in the meta-position to the phosphorus atom.

The following are examples of especially preferred ligands of formula VI:
(S)-(6,6'-Dimethyl-2,2'-biphenylylene)bis(diphenylphosphine):
(S)-(6,6'-dimethyl-2,2'-biphenylylene)bis(di-p-tolylphosphine).

The ligands of formulas VI and VII are known compounds, fox example, from European Publication No. 104 375 or from Japanese Patent Application No. 136 605/1978.

The ruthenium catalysts of formula V can be prepared in a known matter. They can be prepared, for example, by reacting a ruthenium complex of the formula

[Ru(Z¹)₂L¹ₘ]ₙ·(H₂O)ₚ   VIII wherein Z¹ is halogen or a residue of the formula A¹-COO⁻, A¹ is halogenated lower alkyl, L¹ is a neutral ligand, m is the number 0, 1, 2 or 3, n is the number 1 or 2 and p is the number 0 or 1, with a chiral diphosphine ligand of formula VI or VII, or by reacting a ruthenium complex of the formula Ru(CF₃COO)₂L   IX wherein L has the above significance,
with a salt which contains the anion Z, wherein Z has the above significance.

The ruthenium catalysts of formula Va can also be prepared in a known manner, for example in analogy to the procedure of K. Mashima et al., J. Chem. Soc. Chem. Commun. 1989, 1208–1210.

The term "neutral ligand" denotes a readily exchangeable ligand such as, a diolefin, for example, norbornadiene, 1,5-cyclooctadiene and the like, or a nitrile, for example, acetonitrile, benzonitrile and the like. When m is the number 2 or 3, the ligands can be the same or different.

The ruthenium complexes of formula VIII which are used as starting materials are known substances or analogues of known substances which can be obtained readily in an analogous manner to the production of the known substances, for example in accordance with Albers, M. O. et al., J. Organomet. Chem., 272 (1984) C62–C66.

The reaction of a ruthenium complex of formula VIII with a chiral diphosphine ligand of formula VI or VII can be carried out in a known manner. The reaction can be conveniently effected in an inert organic solvent. As examples of such solvents, there can be named, for example, ethers such as tetrahydrofuran or dioxane, ketones such as, acetone, lower alcohols such as, for example, methanol, ethanol and the like., halogenated hydrocarbons such as methylene chloride, chloroform and the like, or mixtures of such solvents. Moreover, the reaction can be effected at a temperature in the range from about 0° C. to about 100° C. and preferably between about 15° C. and about 60° C., but with the strict exclusion of oxygen.

The reaction of a ruthenium complex of formula IX with a salt which contains the anion Z can be effected in a known manner. The term "a salt which contains the anion Z" is within the scope of the invention, for example, ammonium salts, alkali metal salts or other suitable metal salts. In order to improve the solubility of such salts, crown ethers can also be added in certain instances.

In the performance of the previously mentioned asymmetric hydrogenations, the complexes of formula V can first be produced and then added to a solution of the substance to be hydrogenated. Alternatively, the complexes can, however, also be produced in situ in the presence or absence of a substance to be hydrogenated.

The asymmetric hydrogenation can be effected in a suitable organic solvent which is inert under the reaction conditions. As such solvents there can be named, in particular, lower alcohols such as methanol or ethanol or mixtures of such alcohols with halogenated hydrocarbons such as methylene chloride, chloroform and the like or with cyclic ethers such as tetrahydrofuran or dioxane and the like. The ratio of ruthenium to ligand L conveniently lies in the range from about 0.5 to about 2 mol, preferably at about 1 mol of ruthenium per mol of ligand. The ratio of ruthenium in the complexes of formula V or Va to the substances to be hydrogenated conveniently lies in the range of from about 0.005 and about 2 mol%, preferably between about 0.01 and about 0.1 mol%.

The asymmetric hydrogenation with the complexes of formula V or Va is conveniently effected at a temperature in the range of from about 50° C. to about 200° C., preferably of about 80° C. to about 160° C. This hydrogenation is also conveniently effected under pressure, preferably at a pressure of about 5 to about 200 bar, preferably of about 20 to about 100 bar.

The compounds of formula II in the (E)-form as well as the mixture comprising the compounds of formula II in the (E)-form, of formula I in the (Z)-form and of formula III, which are used as starting materials in the process in accordance with the invention, can be prepared in a known manner. Thus, the mentioned mixture can be prepared, for example, by reacting a compound of the formula

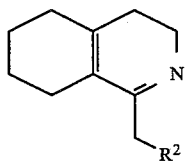 X wherein $R^2$ has the above significance, with an acylating agent of the formula

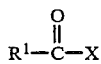 XI wherein $R^1$ has the above significance and X is halogen or a residue of the formula

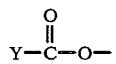

in which Y is lower alkyl.

The acylation of a compound of formula X with an acylating agent of formula XI can be effected in an inert organic solvent in the presence of a base and at a temperature in the range of from about −20° C. to about 50° C., preferably of about 0° C. to about 20° C. Suitable solvents are aprotic solvents such as aliphatic or aromatic hydrocarbons, for example, hexane, benzene, toluene and the like., as well as ethers, for example, diethyl ether, tetrahydrofuran, dioxane and the like. As bases, there can be used here amines such as triethylamine or pyridine as well as alkali metal salts and alkaline earth metal salts of organic acids such as sodium formate, sodium acetate and the like. From thus-obtained mixtures of the compounds II (E-form), I (Z-form) and III, there can readily be isolated, for example, by column chromatography, compounds of formula II in the E-form.

The compounds of formula III, which are also used as starting materials in the process in accordance with the invention, can be obtained, for example, by isomerizing compounds of formula II in the E-form. This isomerization can be carried out, for example, in an analogous manner to the previously mentioned isomerization. In this case, the course of the reaction is followed, for example, by gas chromatography and is interrupted at the maximum concentration of compound III.

The Examples which follow further illustrate the invention. In the Examples, the chosen abbreviations have the following meaning:
GC:gas chromatography
THF:tetrahydrofuran
BIPHEMP:(S)-(6,6-dimethyl-biphenylylene)bis(diphenyl-phosphine)
COD:1,5-cyclooctadiene

EXAMPLE 1

A solution of 0.2 g of (E)-2-acetyl-1,2,3,4,5,6,7,8-octahydro-1-(p-methoxybenzylidene)isoquinoline and 8.7 mg of dichlorobis(acetonitrile)palladium(II) in 10 ml of dry tetrahydrofuran was heated at reflux for 7 hours under argon. The yellow solution was evaporated at 15 mbar and the residue was dissolved in diethyl ether. In order to separate the catalyst, the ether solution was filtered through a thin layer of silica gel. After evaporation of the filtrate there was obtained 0.19 g of (Z)-2-acetyl-1,2,3,4,5,6,7,8-octahydro-1-(p-methoxybenzylidene)-isoquinoline with a m.p. of 101–102° C.; content according to GC 96%:

The (E)-2-acetyl-1,2,3,4,5,6,7,8-octahydro-1-(p-methoxybenzlidene)isoquinoline used as the starting material was prepared as follows:

164 g (1.61 mol) of acetic anhydride were added at 0–3° C. under argon during 20 minutes to a stirred solution of 0.80 mol of crude 1-(p-methoxybenzyl)-3,4,5,6,7,8-hexahydroisoquinoline [obtained according to 0. Schnider et al., Helv. Chim. Acta 33, 1437 (1950)]in 2 liters of toluene. Subsequently, 204 g (2.01 mol) of triethylamine were added during 30 minutes. The mixture was stirred overnight and the temperature was allowed to rise to 15°–20° C. After cooling to 5° C., the reaction mixture was washed in succession with ice-water, 2N HCl, ice-water, 2N NaOH, ice-water and saturated brine. The organic phase was dried over sodium sulfate and then concentrated, whereby 205 g of a red-brown oil were obtained. After column chromatography and crystallization from methanol, there were obtained 41.3 g of (E)-2-acetyl-1,2,3,4,5,6,7,8-octahydro-1-(p-methoxybenzylidene)isoquinoline which was pure according to thin-layer chromatography and gas chromatography. M.p. 74.5°–76° C.

EXAMPLE 2

The isomerizations of (E)-2-acetyl-1,2,3,4,5,6,7,8-octahydro-1-(p-methoxybenzylidene)isoquinoline which are set forth in Table 1 were carried out in an analogous manner to Example 1:

TABLE 1

| Catalyst 5 mol % | Solvent c = 2% | T (°C.) | Time (h) | Product % (Z) | % (E) |
|---|---|---|---|---|---|
| HBr | Methanol | 65 | 7 | 78 | <1 |
| p-Toluenesulfonic acid | Toluene | 111 | 16 | 89 | <1 |
| p-Toluenesulfonic acid | Methanol | 65 | 16 | 95 | <1 |
| Phenylsulfinic acid | Methanol | 65 | 16 | 81 | 7 |
| None | Acetic acid | 118 | 7 | 85 | 7 |
| None | CH$_2$Cl$_2$ | 100 a) | 22 | 91 | <1 |
| BF$_3$ etherate | Benzene | 80 | 7 | 95 | <1 |
| TiCl$_4$ | THF | 66 | 6 | 92 | <1 |
| PdCl$_2$(CH$_3$CN)$_2$ | CH$_2$Cl$_2$ | 25 | 16 | 94 | <1 |
| PdCl$_2$(CH$_3$CN)$_2$ | THF | 66 | 16 | 96 | <1 |
| RhCl$_3$ hydrate | THF | 66 | 7 | 96 | <1 |
| RuCl$_3$ hydrate | THF | 66 | 7 | 89 | <1 |
| Iodine | CH$_2$Cl$_2$ | 41 | 7 | 89 | <1 |
| Iodine | Toluene | 111 | 16 | 88 | <1 |
| TEMPO b) | Toluene | 111 | 16 | 82 | <1 | a) 20 bar of argon
b) 2,2,6,6-Tetramethyl-1-piperidinyloxyl a) 20 bar of argon  b) 2,2,6,6-Tetramethyl-1-piperidinyloxyl

EXAMPLE 3

A solution of 0.2 g of 2-acetyl-1-(p-methoxybenzyl)-2,3,4,6,7,8-hexahydroisoquinoline and 2.5 mg of acetyl chloride in 10 ml of dry methanol was heated at reflux under argon for 16 hours. The reaction mixture was evaporated and the residue was dissolved in diethyl ether. The ether solution was washed with saturated sodium bicarbonate solution, water and saturated sodium chloride solution, dried over sodium sulfate and evaporated in a vacuum on a rotary evaporator. The residue consisted of 95% (Z)-2-acetyl-1,2,3,4,5,6,7,E-octahydro-1-(p-methoxybenzylidene)isoquinoline according to GC. Recrystallization from methanol yielded 140 mg of pure (Z)-isomer: m.p. 101°–102° C.

The 2-acetyl-1-(p-methoxybenzyl)-2,3,4,6,7,8-hexahydroisoquinoline used as the starting material was prepared as follows:

A solution of 2.1 g of (E)-2-acetyl-1,2,S,4,5,6,7,8-octahydro-1-(p-methoxybenzylidene)isoquinoline (prepared according to Example 1) in 120 ml of methylene chloride was heated at reflux for 2 hours under argon. The solvent was then distilled off at 30° C./20 mbar. The residue, 2.3 g of a colorless oil, contained 61% of the desired product according to GC. Column chromatography and crystallization from isopropyl ether gave 700 mg of 2-acetyl-1-(p-methoxybenzyl)-2,3,4,6,7,8-hexahydroisoquinoline, which was pure according to thin-layer chromatography and gas chromatography, as white crystals. M.p. 48°–50° C.

EXAMPLE 4

A solution of 8.4 g of iodine (0.033 mol) in 400 ml of methylene chloride was added dropwise under argon to a solution of 98.1 g (0.330 mol) of a mixture of (E)-2-acetyl-1,2,3,4,5,6,7,8-octahydro-1-(p-methoxybenzylidene) isoquinoline, (Z)-2-acetyl-1,2,3,4,5,6,7,S-octahydro-1-(p-methoxybenzylidene)isoquinoline and 2-acetyl-1-(p-methoxybenzyl)-2,3,4,6,7,8-hexahydroisoquinoline in 2 liters of methylene chloride. After stirring the resulting red solution overnight at room temperature, it was washed once with 250 ml of a 0.5N sodium thiosulfate solution and once with 250 ml of brine. The aqueous extracts were back-washed twice with the same 250 ml aliquot of methylene chloride. The combined organic extracts were dried over sodium sulfate and concentrated on a rotary evaporator, whereby there were obtained 98.9 g of a red oil. This oil contained 93.3% of (Z)-2-acetyl-1,2,3,4,5,6,7,8-octahydro-1-)(p-methoxybenzylidene)-isoquinoline according to GC.

The crude (Z)-isomer was heated at reflux while stirring with 650 ml of diisopropyl ether until all material had dissolved with the exception of a small amount of dark residue. The hot solution was decanted off and kept hot. The residue was extracted with 300 ml of diisopropyl ether for one hour and the solution was decanted. The hot solutions were combined and stirred with 2 g of active charcoal for 15 minutes. After filtration, the yellowish solution was concentrated at 40° C. under reduced pressure to a volume of about 500 ml. The crystal-lization of the product, which had already set in during the distillation, was continued at 0° C. overnight. The crystals were then removed by filtration, washed twice with 60 ml of cold (−20° C.) diisopropyl ether and dried at 30° C./0.01 mbar. There were obtained 68.8 g of (Z)-2-acetyl-1,2,3,4,5,6,7,8-octahydro-1-(p-methoxybenzylidene)isoquinoline quinoline as white crystals with a melting point of 100°–102° C.

The mixture of isomers used as the starting material was prepared as follows:

81.5 g (0.805 mol) of triethylamine and 2 l of toluene were placed in a 4.5 l four-necked flask provided with a thermometer, a 500 ml dropping funnel, a mechanical stirrer and a gas inlet tube and the solution was cooled to 0°–2° C. Then, under nitrogen and at 0°–3° C., there were added in succession first during 5 minutes 500 ml of a solution of 0.8 mol of 1-(p-methoxybenzyl)-3,4,5,6,7,8-hexahydroisoquinoline hydrochloride [prepared according to O. Schnider et al., Helv. Chim. Acta 33, 1437 (1950)]in toluene, then during 15 minutes 164.4 g (1.610 mol) of acetic anhydride and thereupon during 15 minutes 203.6 g (2.012 mol) of triethylamine. The ice bath was subsequently removed and the yellow solution was stirred at 20° C. for 20 hours. The reaction mixture was cooled to 2° C. and extracted in succession with the following cold solutions:

once with 1 l and twoce with 0.5 l of ice-water,
once with 200 ml and twice with 100 ml of 2N sodium hydroxide solution,
once with 0.5 l of ice-water,
once with 0.5 l and twice with 0.3 l of 2N hydrochloric acid,
three times with 0.5 l of water and
once with 0.5 l of brine.

Each aqueous extract was back-washed twice with the same 0.3 l aliquots of toluene.

The combined toluene solutions were dried over magnesium sulfate and evaporated at 40° C./20 mbar and there were obtained 234.1 g (97.6%) of a red-brown oil. According to thin-layer chromatography, this consisted of a mixture of (E)-2-acetyl-1,2,3,4,5,6,7,8-octahydro-1-(p-methoxybenzylidene)isoquinoline, (Z)-2-acetyl-1,2,3,4,5,6,7,8,octahyro-1-(p-methoxybenzylidene)isoquinoline and 2-acetyl-1-(p-methoxybenzyl)-2,3,4,6,7,8-hexahydroisoquinoline in the ratio 40:45:15. In order to remove any polar impurities which may still have been present, the crude material was filtered through a short column (10 cm diameter) of 1 kg of silica gel (0.04–0.063 mm) using 7 liters of benzene/ethyl acetate (3:1, v/v) as the eluent. By concentration of the eluate there were obtained 196.2 g (81.9%) of a red-brown oil which, according to thin-layer chromatography, consisted only of the mentioned three components.

EXAMPLE 5

A 500 ml autoclave was charged in a glove box with 2 g (6.73 mmol) of (Z)-2-acetyl-1,2,3,4,5,6,7,8-octahydro-1-(p-methoxybenzylidene)isoquinoline (prepared according to any one of Examples 1–4), 170 ml of methanol and 1.3 mg (0.0017 mmol; S/Ru =4000) of Ru(CH$_3$COO)$_2$(BIPHEMP) as the catalyst. The hydrogenation was carried out at 100° C. and 35 bar for 24 hours. The hydrogenation solution was evaporated and the residue was dissolved in diethyl ether. After separation of the catalyst over silica gel and evaporation of the filtrate, there were obtained 1.98 g of (S)-2-acetyl-1 -(p-methoxybenzyl) -1,2,3,4,5,6,7,8-octahydroisoquinoline of 98.3% e.e., which was recrystallized from diisopropyl ether. $[\alpha]_D^{20}= +53°$ (c=1 in CH$_3$OH); 100% e.e., m.p. 80°–81.5° C.

In order to determine the e.e. value, the product was hydrolyzed in a mixture of ethylene glycol and 40% aqueous potassium hydroxide solution at 170° C. for 18 hours. The amine formed was converted with (−)-camphanoyl acid chloride in pyridine/4-dimethylaminopyridine to give a mixture of the diastereomeric amides and the mixture was analyzed by GC.

EXAMPLE 6

A 500 ml autoclave was charged in a glove box with 2.0 g (6.73 mmol) of (Z)-2-acetyl-1-(p-methoxybenzylidene)-1,2,3,4,5,6,7,8-tetrahydroisoquinoline, 140 ml of methanol, 28 ml of methylene chloride and Ru(CF$_3$COO)$_2$(BIPHEMP) [prepared in situ from 3.7 mg of BIPHEMP and 3.0 mg of [Ru(CF$_3$COO)$_2$(COD)]$_2$H$_2$: E. Singleton et al. J. Organomet. Chem. 272 (1984) C62–C66]as the catalyst. The hydrogenation was carried out at 160° C. and 60 bar for 1 hour, whereafter the conversion amounted to 100%. The product was isolated analogously to Example 5. There were obtained 1.9 g of (S)-2-acetyl-1-(p-methoxybenzyl)-1,2,3,4,5,6,7,8-octahydroisoquinoline; 96.3% e.e. The e.e. value was determined in an analogous manner to Example 5.

EXAMPLE 7

A 500 ml autoclave was charged in a glove box with 2.0 g (6.7 mmol) of (E)-2-acetyl-1-(p-methoxybenzylidene)-1,2,3,4,5,6,7,8-tetrahydroisoquinoline, 140 ml of methanol, 28 ml of methylene chloride and Ru(X)$_2$-(BIPHEMP) as the catalyst. The hydrogenation was carried out under the conditions indicated in Table 2. The product, (S)-2acetyl-1-(p-methoxybenzyl)-1,2,3,4,5,6,7,8-octahydroisoquinoline, was isolated and analyzed analogously to Example 5. The e.e. value was determined in an analogous manner to Example 5.

TABLE 2

| X | S/Ru | T (°C.) | (bar) | Conversion % | Time (h) | e.e % (S) |
|---|------|---------|-------|--------------|----------|-----------|
| CH$_3$COO a) | 2000 | 100 | 60 | 95.4 | (5) | 93.8 |
| CF$_3$COO | 2000 | 100 | 35 | 99.4 | (22) | 95.6 |

TABLE 2-continued

| X | S/Ru | T (°C.) | (bar) | Conversion % | Time (h) | e.e % (S) |
|---|------|---------|-------|--------------|----------|-----------|
| Cl b) | 4000 | 100 | 35 | 90 | (42) | 97.3 | a) Catalyst prepared in situ from Ru(CF$_3$COO)$_2$BIPHEMP and 2 mol equivalents of sodium acetate
b) Catalyst prepared in situ from Ru(CH$_3$COO)$_2$BIPHEMP and 2 mol equivalents of HCl

Example 8

A 500 ml autoclave was charged in a glove box (O$_2$ content <1 ppm) with 2.0 g (6.73 mmol) of (Z)-2-acetyl-1-(p-methoxybenzylidene)-1,2,3,4,5,6,7,8-octahydroisoquinoline, 140 ml of methanol and a catalyst solution of 1.53 mg of [Ru{(S)-BIPHEMP}Cl(p-cymene]BF$_4$ (prepared in analogy to K. Mashima et al., J. Chem. Soc. Chem. Commun. 1989, 1208–1210) in 30 ml of methanol. The hydrogenation was effected at 100° C. and 35 bar while stirring intensively. After 18 hours, the conversion amounted to 99.4%. The hydrogenation solution was worked-up analogously to Example 5. There were obtained 1.94 g of (S)-2-acetyl-1-(p-methoxybenzyl)-1,2,3,4,5,6,7,8-oxtahydroisoquinoline: hydroisoquinoline: e.e. 97.7%.

We claim:
1. A process for the preparation of an isoquinoline derivative of formula I in the Z-form

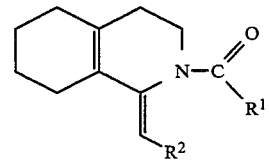

wherein R$^1$ is lower alkyl, aryl, or aryl-lower alkyl and R$^2$ is phenyl or p-methoxyphenyl
which comprises isomerizing at least one isoquinoline derivative of the formula

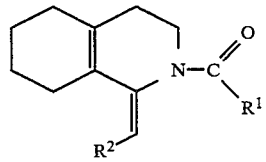
E-form II or

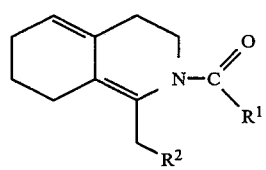
III alone or both together in a mixture with the isoquinoline derivative of formula I
wherein R$^1$ is lower alkyl, aryl, or aryl-lower alkyl and R$^2$ is phenyl or p-methoxyphenyl
in a solvent selected from the group consisting of aromatic hydrocarbons, alcohols having 1–3 C atoms, ethers or chlorinated hydrocarbons, at a temperature of between room temperature and 200° C., for at least 6 hours, and if desired, recovering the resulting isoquinoline derivative.

2. A process according to claim 1, wherein the thus-obtained isoquinoline derivative of the formula I in the Z-form

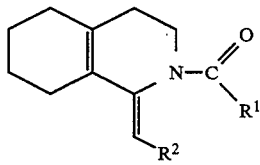

I wherein $R^1$ and $R^2$ are as described above, is asymmetrically hydrogenated to give a compound of the formula

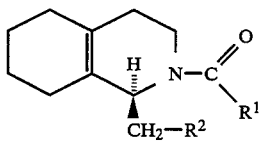

IV wherein $R^1$ and $R^2$ as described above.

3. A process according to claim 1, wherein the isomerization of a compound of formula II in the E-form, of a compound of formula III or of a mixture of isoquinoline derivatives of formulas II (E-form), I (Z-form) and III is carried out by heating in a chlorinated hydrocarbon or in a solvent which contains a chlorinated hydrocarbon.

4. A process according to claim 1, wherein the isomerization of a compound of formula II in the E-form, of a compound of formula III or of a mixture of isoquinoline derivatives of formulas II (E-form), I (Z-form) and III is carried out catalytically.

5. A process according to claim 3, wherein the isomerization is carried out by heating to a temperature in the range of from about 50° C. to about 120° C.

6. A process according to claim 5, wherein methylene chloride, chloroform or 1,2-dichloroethane is used as the chlorinated hydrocarbon in the isomerization.

7. A process according to claim 6, wherein a lower alcohol with 1 to 5 carbon atoms is used as the solvent in the isomerization, and the reaction temperature is in the range of from about the reflux temperature to about 150° C.

8. A process according to claim 4, wherein an acid, especially a hydrohalic acid, iodine or a transition metal complex is used as the catalyst for the catalytic isomerization.

9. A process according to claim 2, wherein the asymmetric hydrogenation of a compound of formula I in the Z-form is carried out in the presence of a ruthenium catalyst of formula V or Va:

$$Ru(Z)_2L \quad \quad V$$

or $$[Ru(Z^2)_{2-n}(L)(X)]Z_n^3 \quad \quad Va$$

wherein Z is halogen or a residue of the formula A-COO— in which A is lower alkyl, aryl, halogenated lower alkyl or halogenated aryl, $Z^2$ is halogen, X is benzene, hexamethylbenzene or p-cymene, $Z^3$ is halogen, $BF_4$, $ClO_4$ or $B(phenyl)_4$, n is the number 1 or 2 and L is a ligand of formula VI or VII:

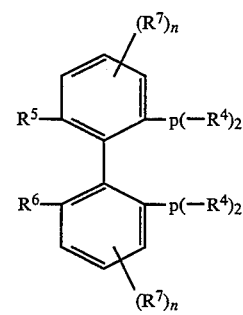

VI wherein $R^4$ is phenyl, $R^5$ and $R^6$ which can be the same or different, are hydrogen, lower alkyl, lower alkoxy, di-lower alkylamino or protected hydroxymethyl or $R^5$ and $R^6$ taken together are the group

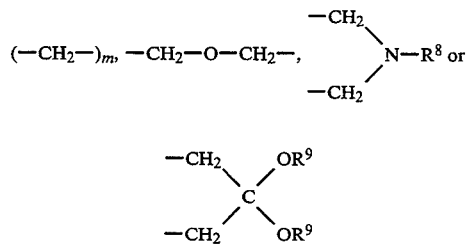

in which m is a number 3 to 5, $R^8$ is lower alkyl, phenyl or benzyl and $R^9$ is lower alkyl or both $R^9$'s taken together are di- or trimethylene, $R^7$ is methyl, lower alkoxy, di-lower alkylamino or fluorine and n is the number 0, 1, 2 or 3;

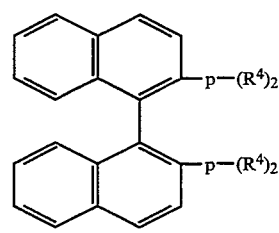

VII wherein $R^4$ is phenyl and the naphthalene rings are unsubstituted or substituted in the ortho-position with methyl, ethyl, halogen, di-lower alkylamino or lower alkoxy.

10. A process according to claim 9, wherein the asymmetric hydrogenation is carried out at a temperature in the range of from about 50° C. to about 200° C.

11. A process according to 9, wherein the asymmetric hydrogenation is carried out at a temperature in the range of from about 80° C. to about 160° C.

12. A process for the preparation of an isoquinoline derivative of formula I in the Z-form

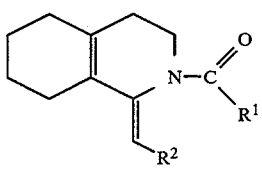
I wherein R¹ is lower alkyl, aryl or aryl-lower alkyl and R² is phenyl or p-methoxyphenyl
which comprises isomerizing an isoquinoline derivative of formula II

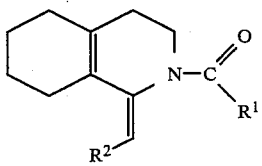
II wherein R¹ and R² are as above
in a solvent selected from the group consisting of aromatic hydrocarbons, alcohols having 1-3 C atoms, ethers or chlorinated hydrocarbons, at a temperature of between room temperature and 200° C. for at least 6 hours, and if desired, recovering the resulting isoquinoline derivative.

13. A process for the preparation of an isoquinoline derivative of formula I in the Z-form

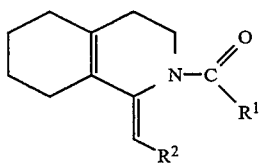
I wherein R¹ is lower alkyl, aryl or aryl-lower alkyl and R² is phenyl or p-methoxyphenyl
which comprises isomerizing an isoquinoline derivative of formula III

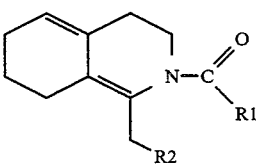
III wherein R¹ and R² are as above
in a solvent selected from the group consisting of aromatic hydrocarbons, alcohols having 1-3 C atoms, ethers or chlorinated hydrocarbons, at a temperature of between room temperature and 200° C. for at least 6 hours, and if desired, recovering the resulting isoquinoline derivative.

14. A process for the preparation of an isoquinoline derivative of formula I in the Z-form

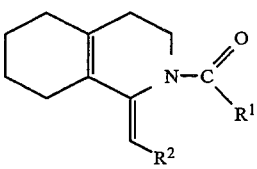
I wherein R¹ is lower alkyl, aryl or aryl-lower alkyl and R² is phenyl or p-methoxyphenyl
which comprises isomerizing a mixture of the isoquinoline derivatives of formula II, formula III and formula I

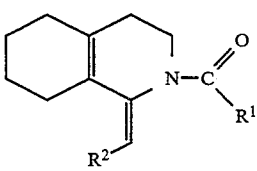
II

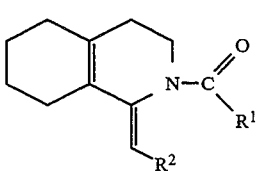
I

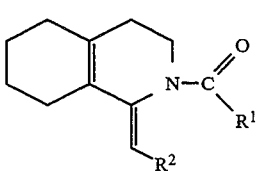
III wherein R¹ and R² are as above,
in a solvent selected from the group consisting of aromatic hydrocarbons, alcohols having 1-3 C atoms, ethers or chlorinated hydrocarbons, at a temperature of between room temperature and 200° C. for at least 6 hours, and if desired, recovering the resulting isoquinoline derivative.

* * * * *